US011628471B2

(12) United States Patent
Taffler

(10) Patent No.: US 11,628,471 B2
(45) Date of Patent: *Apr. 18, 2023

(54) ULTRASONIC IMAGING AND ENERGY DELIVERY DEVICE AND METHOD

(71) Applicant: Acoustiic Inc., Pacific Palisades, CA (US)

(72) Inventor: Sean Taffler, Pacific Palisades, CA (US)

(73) Assignee: Acoustiic inc., Pacific Palisades, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/362,386

(22) Filed: Jun. 29, 2021

(65) Prior Publication Data

US 2021/0323028 A1    Oct. 21, 2021

Related U.S. Application Data

(63) Continuation of application No. 16/104,786, filed on Aug. 17, 2018, now Pat. No. 11,065,643.

(51) Int. Cl.
*B06B 1/02* (2006.01)

(52) U.S. Cl.
CPC .......... *B06B 1/0215* (2013.01); *B06B 1/0269* (2013.01)

(58) Field of Classification Search
CPC ... B06B 1/0215; B06B 1/0269; A61B 8/4281; A61B 8/481; A61B 8/485; A61B 8/486;
(Continued)

(56) References Cited

U.S. PATENT DOCUMENTS 11,065,643 B2 *   7/2021   Taffler ................ A61B 8/4281
2009/0177085 A1   7/2009   Maxwell
(Continued)

FOREIGN PATENT DOCUMENTS

EP    3836842 A1 *   6/2021   ............ A61B 8/085
GB    2511556 A      9/2014
(Continued)

OTHER PUBLICATIONS

Invitation to Pay Additional Fees and Where Applicable Protest Fee for Application No. PCT/US2019/046873, dated Nov. 7, 2019, 14 pages.
(Continued)

*Primary Examiner* — Daniel Pihulic
(74) *Attorney, Agent, or Firm* — Ian Harrison; Butzel Long

(57) ABSTRACT

An ultrasonic device includes a driving circuit to provide drive power, a first transducer array to generate ultrasonic waves, the first transducer array being connected to receive power from the driving circuit, and a second transducer array to detect reflected or elicited ultrasonic waves incident on the device from a target and generate a signal based on those waves, the second transducer array being acoustically transmissive and disposed over the first transducer array such that the generated ultrasonic waves pass through the second transducer array. The second array is tuned to operate on top of the first. The functions of the two arrays may be reversed and the array tuned to operate with the first array receiving and the second array transmitting.

27 Claims, 4 Drawing Sheets

(58) Field of Classification Search
CPC .. A61B 8/488; A61B 8/54; A61B 8/13; A61B 8/4477; A61B 8/4488; A61B 8/4494; A61B 8/085; A61B 8/56; A61N 7/00; A61N 2007/0078; A61N 2007/0095
See application file for complete search history.

(56) References Cited

U.S. PATENT DOCUMENTS

| | | |
|---|---|---|
| 2012/0172721 A1 | 7/2012 | Curra |
| 2017/0311808 A1 | 11/2017 | Thornton |
| 2018/0028149 A1 | 2/2018 | Wang |
| 2020/0055085 A1* | 2/2020 | Taffler .................. B06B 1/0215 |
| 2021/0323026 A1* | 10/2021 | Taffler .................... A61B 8/085 |
| 2021/0323027 A1* | 10/2021 | Taffler ..................... A61B 8/13 |
| 2021/0323028 A1* | 10/2021 | Taffler .................... A61B 8/085 |

FOREIGN PATENT DOCUMENTS

| | | | |
|---|---|---|---|
| WO | 20161797091 | 11/2016 | |
| WO | 2020037237 A1 | 2/2020 | |
| WO | WO-2020037237 A1 * | 2/2020 | ............. A61B 8/085 |

OTHER PUBLICATIONS

International Search Report and Written Opinion for Application No. PCT/US2019/046873, dated Jan. 17, 2020, 18 pages.

* cited by examiner

ULTRASONIC IMAGING AND ENERGY DELIVERY DEVICE AND METHOD

BACKGROUND

Conventional ultrasonic imaging and energy delivery devices are typically constructed including a collection of N transduction elements ("elements") to produce acoustic waves, and in the case of imaging devices, a switch mechanism to enable changing the function of the elements to a receiving mode to allow for reception of incident waves. The elements convert electrical signals into pressure (acoustic) waves that propagate at ultrasonic frequencies. Typically, individual elements (and corresponding control switches) are arranged in an array format. The array structure may be designed as a one-dimensional or two-dimensional array. The array of elements may be synchronized to project sound through a target object. In the case of imaging, after projecting the sound the elements are then switched to operate in a receiving mode in order to convert incident acoustic energy into an electrical signal that can be processed using analogue circuits or algorithms performed by a processor (e.g. computer, microprocessor, GPU, FPGA, ASIC or equivalent chip/hardware or circuit) to create an image.

BRIEF SUMMARY

According to an embodiment of the disclosed subject matter, an ultrasonic device includes a driving circuit to provide drive power, a first transducer array to generate ultrasonic waves toward a target, the first transducer array being connected to receive power from the driving circuit, and a second transducer array to detect reflected or elicited ultrasonic waves traveling toward the ultrasonic device from the target, and to generate a signal based on the detected ultrasonic waves, the second transducer array being acoustically transmissive and disposed over the first transducer array such that the generated ultrasonic waves pass through the second transducer array.

The ultrasonic device can include a matching/de-matching layer, disposed between the first transducer array and the second transducer array. The matching/de-matching layer can have a material and thickness that allows the generated ultrasonic waves to pass through and impede the reflected or elicited ultrasonic waves from reaching the first transducer array.

The matching/de-matching layer can be constructed of a material having greater or equal thermal conductivity than the first transducer array and the second transducer array.

The matching/de-matching layer can be constructed of a material having less thermal conductivity than the first transducer array and the second transducer array.

Transducer elements that form the second transducer array can have a different frequency response than transducer elements that form the first transducer array.

Transducer elements that form the second transducer array can have a different steering response than transducer elements that form the first transducer array.

Transducer elements that form the second transducer array can have a different sensitivity response than transducer elements that form the first transducer array.

Transducer elements that form the second transducer array can be of a different size and/or pitch in one or more axes than transducer elements that form the first transducer array.

Transducer elements that form the second transducer array can be approximately ¼ the size of transducer elements that form the first transducer array.

Transducer elements in the second transducer array can be arranged in a repeating pattern comprising four transducer elements of the second transducer array disposed substantially over a single transducer element of the first transducer array.

The generated ultrasonic waves can include a first pulse to deliver therapeutic energy to a region in the target and/or followed by a second pulse having a lower energy level than the first pulse to deliver an ultrasonic imaging wave to the region. The detected ultrasonic waves can include waves from the ultrasonic imaging wave reflected or elicited from the target region. The second transducer array can generate the signal based on the detected waves, and the signal can carry data to create an image of the target region.

The generated ultrasonic waves from the first transducer array can deliver therapeutic energy to a region in the target, and the second transducer array can detect incident waves reflected or elicited from the region and generate the signal based on the incident waves, the signal carrying data to create a digital image of the target region or data that indicates a material property of the target region.

The first transducer array can generate the ultrasonic waves to elicit histotripsy or boiling histotripsy.

The first transducer array can generate ultrasonic waves within a first frequency band, and transducer elements in the second transducer array can be substantially less sensitive to ultrasonic waves within the first frequency band than transducer elements in the first transducer array, such that the second transducer array detects incident ultrasonic waves within a second frequency band different from the first frequency band.

The first frequency band can have a central frequency of approximately 1 MHz and the second frequency band has a central frequency of approximately 2 MHz.

The first transducer array can be a phased array.

The driving circuit can be disposed on a first side of the first transducer array, and the second transducer array can be disposed on a second side of the transducer array opposite the first side.

The driving circuit can be substantially acoustically transparent and disposed between the first transducer array and the second transducer array.

According to another embodiment of the disclosed subject matter, a method of conducting ultrasonic therapy or ultrasonic imaging using an ultrasonic device includes disposing an acoustically transmissive second transducer array over a first transducer array such that ultrasonic waves generated by the first transducer array substantially pass through the second transducer array, providing power to the first transducer array, the power causing the first transducer array to generate ultrasonic waves toward a target, detecting, with the second transducer array, reflected or elicited ultrasonic waves from the target, generating a signal, with the second transducer array, based on the detection, and creating a digital image of the target region based on the signal or determining a material property of the target based on signal.

The method can further include impeding the reflected or elicited ultrasonic waves from reaching the first transducer array by disposing a matching/de-matching layer between the first transducer array and the second transducer array.

The method can further include transmitting heat, generated by the first and second transducer arrays, from inner regions of the arrays to edge regions of the arrays by disposing a thermally conductive layer between, and in contact with at least one of, the first and second transducer arrays.

The method can further include delivering therapeutic energy, via the generated ultrasonic waves from the first transducer array, to a target region in a subject.

The method can further include providing power to the first transducer array at least in part by providing a first signal to the first transducer array to cause the first transducer array to send ultrasonic energy to a target region in a subject, and providing a second signal to the first transducer array, the second signal having a lower energy level than the first signal, to cause the first transducer array to deliver an ultrasonic imaging wave to the target region.

The method can further include detecting, with the second transducer array, incident waves from the ultrasonic imaging wave that are reflected or elicited from the target region, and generating, with the second transducer array the signal based on the incident waves, the signal carrying data to create an image of the target region or data that indicates a material property of the target region.

The method can further include transmitting the generated ultrasonic waves within a first frequency band from the first transducer array, and detecting, with the second transducer array, reflected ultrasonic waves within a second frequency band different from the first frequency band.

In the method the first frequency band can have a central frequency of approximately 1 MHz and the second frequency band can have a central frequency of approximately 2 MHz.

According to another embodiment of the disclosed subject matter an ultrasonic device includes a driving circuit to provide drive power, a first transducer array to generate ultrasonic waves toward a target, the first transducer array being connected to receive power from the driving circuit, and a second transducer array to detect reflected or elicited ultrasonic waves traveling toward the ultrasonic device from the target, and to generate a signal based on the detected ultrasonic waves. The first transducer array can be acoustically transmissive and disposed over the second transducer array such that the detected ultrasonic waves pass through the first transducer array.

The ultrasonic device can further include a matching/de-matching layer, disposed between the first transducer array and the second transducer array, the matching/de-matching layer having a material and thickness that allows the reflected or elicited ultrasonic waves to pass through and impedes the generated ultrasonic waves from reaching the second transducer array.

The matching/de-matching layer can be constructed of a material having greater or equal thermal conductivity than the first transducer array and the second transducer array.

Transducer elements that form the second transducer array can have a different frequency response than transducer elements that form the first transducer array.

Transducer elements that form the second transducer array can have a different steering response than transducer elements that form the first transducer array.

Transducer elements that form the second transducer array can have a different sensitivity response than transducer elements that form the first transducer array.

Transducer elements that form the second transducer array are of a different size in one or more axes than transducer elements that form the first transducer array.

Transducer elements that form the second transducer array are approximately ¼ the size of transducer elements that form the first transducer array.

Transducer elements in the second transducer array can be arranged in a repeating pattern comprising four transducer elements of the second transducer array disposed substantially over a single transducer elements of the first transducer array.

The generated ultrasonic waves can include a first pulse to deliver therapeutic energy to a region in the target followed or preceded by a second pulse having a lower energy level than the first pulse to deliver an ultrasonic imaging wave to the region, the detected ultrasonic waves can include waves from the ultrasonic imaging wave reflected or elicited from the target region, and the second transducer array can generate the signal based on the detected waves, the signal carrying data to create an image of the target region or data that indicates a material property of the target region.

The generated ultrasonic waves from the first transducer array can deliver therapeutic energy to a region in the target, and the second transducer array can detect incident waves reflected or elicited from the region and generates the signal based on the incident waves, the signal carrying data to create a digital image of the target region or data that indicates a material property of the target region.

The first transducer array can generate ultrasonic waves within a first frequency band, and transducer elements in the second transducer array can be substantially less sensitive to ultrasonic waves within the first frequency band than transducer elements in the first transducer array such that the second transducer array detects incident ultrasonic waves within a second frequency band different from the first frequency band.

The first frequency band can have a central frequency of approximately 1 MHz and the second frequency band can have a central frequency of approximately 2 MHz.

The first transducer array can be a phased array.

The driving circuit can be disposed on a first side of the first transducer array, and the second transducer array can be disposed on a second side of the transducer array opposite the first side.

The driving circuit can be substantially acoustically transparent and disposed between the first transducer array and the second transducer array.

According to another embodiment of the disclosed subject matter, an ultrasonic device includes a driving circuit to provide drive power, a first transducer array to generate ultrasonic waves toward a target, the first transducer array being connected to the driving circuit, and a second transducer array to detect reflected or elicited ultrasonic waves reflected back toward the device from the target, the second transducer array being interleaved with the first transducer array and comprising transducer elements that differ from transducer elements in the first transducer array.

Transducer elements that form the second transducer array can have different frequency response than transducer elements that form the first transducer array.

Transducer elements that form the second transducer array can have a different steering response than transducer elements that form the first transducer array.

Transducer elements that form the second transducer array can have different sensitivity response than transducer elements that form the first transducer array.

Transducer elements that form the second transducer array can be of a different size in one or more axes than transducer elements that form the first transducer array.

The generated ultrasonic waves can include a first pulse to deliver therapeutic energy to a region in the target followed by a second pulse having a lower energy level than the first pulse to deliver an ultrasonic imaging wave to the region.

The detected ultrasonic waves can include waves from the ultrasonic imaging wave reflected or elicited from the target region, and the second transducer array can generate the signal based on the detected waves, the signal carrying data to create an image of the target region.

The generated ultrasonic waves from the first transducer array can deliver therapeutic energy to a region in the target, and the second transducer array can detect incident waves reflected or elicited from the region and generate the signal based on the incident waves, the signal carrying data to create a digital image of the target region.

The first transducer array can generate ultrasonic waves within a first frequency band, and transducer elements in the second transducer array can be substantially less sensitive to ultrasonic waves within the first frequency band than transducer elements in the first transducer array such that the second transducer array detects incident ultrasonic waves within a second frequency band different from the first frequency band.

The first frequency band can have a central frequency of approximately 1 MHz and the second frequency band can have a central frequency of approximately 2 MHz.

Additional features, advantages, and embodiments of the disclosed subject matter may be set forth or apparent from consideration of the following detailed description, drawings, and claims. Moreover, it is to be understood that both the foregoing summary and the following detailed description are illustrative and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate embodiments of the disclosed subject matter and together with the detailed description serve to explain the principles of embodiments of the disclosed subject matter. No attempt is made to show structural details in more detail than may be necessary for a fundamental understanding of the disclosed subject matter and various ways in which it may be practiced.

DETAILED DESCRIPTION

Figure 1A:
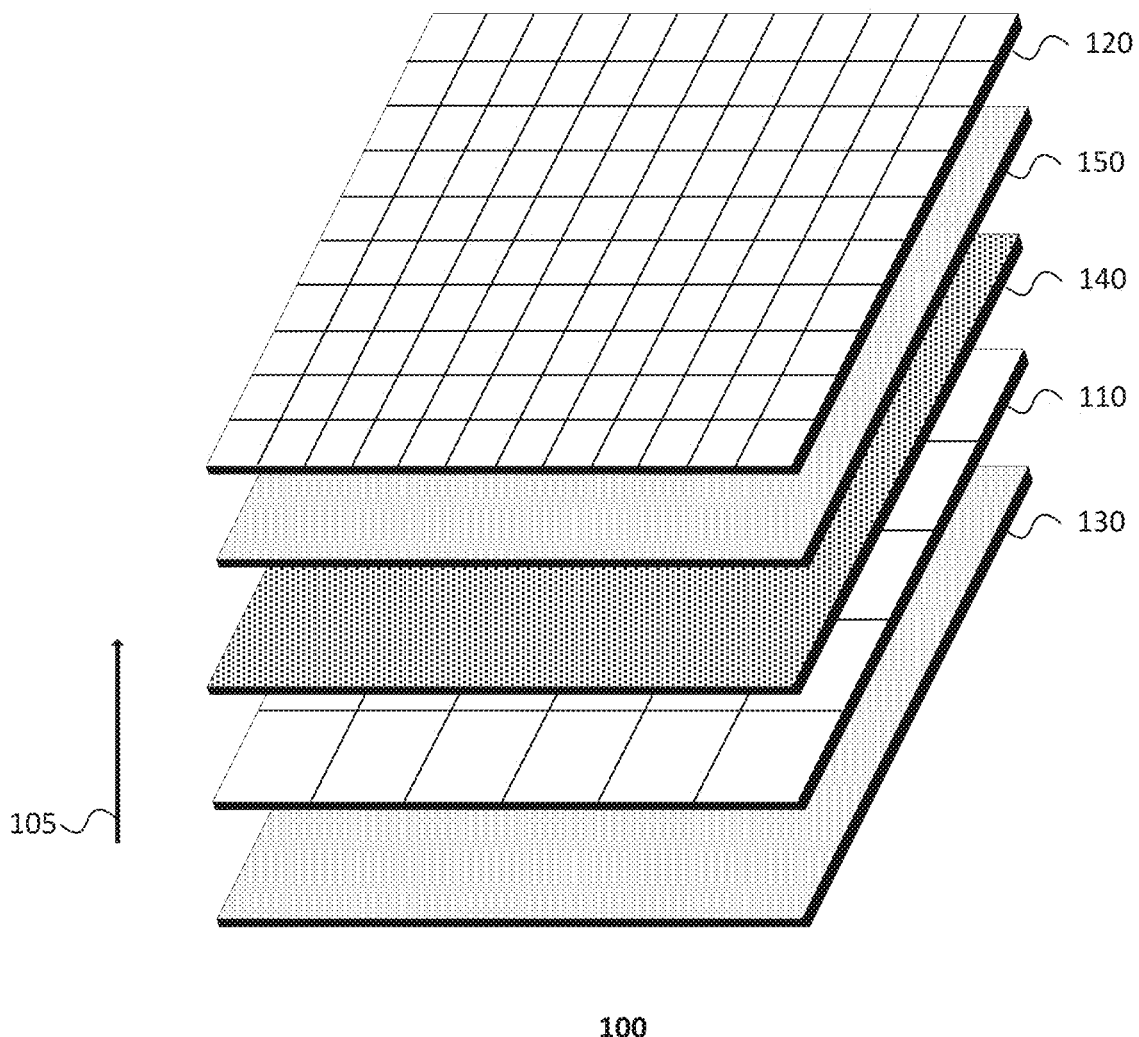
FIG. 1A shows an ultrasonic device according to an embodiment of the disclosed subject matter.

Various aspects or features of this disclosure are described with reference to the drawings, wherein like reference numerals are used to refer to like elements throughout. In this specification, numerous details are set forth in order to provide a thorough understanding of this disclosure. It should be understood, however, that certain aspects of disclosure may be practiced without these specific details, or with other methods, components, materials, etc. In other instances, well-known structures and devices are shown in block diagram form to facilitate describing the subject disclosure.

While, for purposes of simplicity of explanation, the methodologies are shown and described as a series of operations within the context of various flowcharts, it is to be understood and appreciated that in embodiments of the disclosure some operations may occur in different orders and/or concurrently with other operations from that shown and described herein. Moreover, not all illustrated operations may be required to implement a methodology in accordance with the disclosed subject matter.

According to one or more exemplary embodiments, devices and methods are disclosed for applying therapeutic energy at various energy levels (e.g. low-intensity focused ultrasound, high-intensity focused ultrasound, histotripsy, etc.) to a target region in a subject while substantially simultaneously imaging the target region. This is accomplished by utilizing a structure that operates as a projection transducer array separate from, but in conjunction with, a reception transducer array. The configuration of the arrays and the disclosed modes of operations, among other disclosed features, yields numerous improvements and enhanced performance capability compared to conventional device arrangements.

A conventional ultrasonic imaging device typically executes a pulse-echo mode that switches functionality of a transducer array between transmitting and receiving modes. Using this technique, the transducer array generates an acoustic wave that travels into a target area and then switch modes and receives the reflected or elicited wave to convert it into a signal for imaging. However, this configuration necessitates compromises in the design of the transducer array elements. For example, the amount of power that can be generated in the transmitted wave and the drive electronics for doing so are limited due in part to physical constraints of the transducer elements themselves.

Ultrasound transducer arrays commonly use piezo-electric material, such as lead zirconate titanate (PZT) or single crystal, as the transduction element. They require significant voltage to incite the mechanical stress needed to generate the acoustic signal, typically in the order of 10's to 100's of volts. Upon receiving the incident wave, however, the transducer generates a corresponding signal with a voltage typically in the mV range. Accommodating this wide disparity of power in an individual transducer element is challenging and limits options for designing the control electronics for the system. Due to cost and flexibility considerations a custom ASIC would normally be the preferred choice to implement the control electronics needed for a high density system, such as a two-dimensional transducer array. But the requirement for carrying high voltage to activate the transducer elements limits the available process nodes that can be used to fabricate the ASIC. Thus, the advantages of low-voltage, high-speed digital designs for ASICS cannot be leveraged, resulting in specialized design with increased system and design costs.

The pulse-echo mode of operation is also inhibited by inherent operational limitations. A mid-operation time delay (i.e., "a quiescent period") is required to allow the control electronics and transducer array to settle to a quiet state before switching on low noise amplifiers required for reception. The time delay typically occurs as follows: 1) a control circuit (e.g., h-bridge) controls a driving circuit to generate high power signals to generate the ultrasonic wave while a receiving circuit is disconnected; 2) after the wave is generated the control circuit disconnects the driving circuit from the transducer elements; 3) the device waits for a quiescent period to allow resonant voltage in the system to dissipate; and 4) the control circuit connects the transducer elements to the receiving circuit to receive a generated signal. This switching delay eliminates the potential capture of waves that reach the transducer during the delay, thus negatively impacting the distance at which objects can be identified, i.e. the minimum depth that the transducer array can resolve. It also negatively affects the rate at which data can be collected, e.g. the frame rate.

Figure 1B:
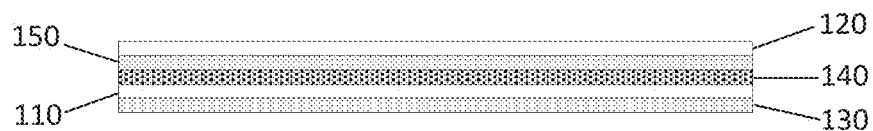
FIG. 1B shows a side view of an ultrasonic device according to an embodiment of the disclosed subject matter.

Many of the limitations imposed by the pulse-echo mode and single array configuration of conventional imaging devices are overcome or reduced in the example embodiment of the disclosed device. FIG. 1A depicts, by way of illustrative and non-limitative example, an exploded view of an embodiment of an ultrasonic therapeutic and/or imaging device 100 having a stacked arrangement according to the disclosed subject matter. FIG. 1B depicts a side view of device 100. Additional layers of varied functionality can be disposed around or within the device.

The disclosed device 100 includes a first transducer array 110 (a "distal array" or "transmit array") to generate the ultrasonic waves, a second transducer array 120 (a "proximal array" or "receive array"), electrically isolated from the first array 110, to detect incident events such as deflection/reflection of ultrasonic waves, a first driving circuit 130 (a "distal electronics" or "transmit electronics") to supply power to the distal array 110 and a second driving circuit 150 (a "proximal electronics" or "receive electronics") to process signals from the proximal array 120 and, in some implementations, provide power as well. The electronics 130, 150 can also include a processor, microprocessor or the like to transmit control signals, execute output timing algorithms, process received signals, etc. The device 100 can include a matching/de-matching layer 140, disposed between the distal array 110 and the proximal array 120. The matching/de-matching layer 140 may be a separate layer or may be combined with a layer for another purpose, such as receive or drive electronics.

The distal array 110 receives drive signals and power from the distal electronics 130, which causes the elements of distal array 110 to generate waves propagating primarily in the direction indicated by arrow 105, e.g. toward a target region in a subject. In other embodiments, the amount of energy traveling in the direction of the arrow may be reduced by an increase in energy being directed in other directions. In an implementation of the disclosed embodiments, the proximal array 120 and the proximal electronics 150 are both acoustically transmissive and substantially allow the generated waves to pass through. The proximal array 120 and the proximal electronics 150 may also be frequency selective to allow waves in particular frequency ranges to pass through while blocking others.

Elements in the proximal array 120 detect incident events caused by the waves generated from the distal array 110. For example, in one disclosed embodiment the proximal array 120 elements convert waves reflected back from the target region into corresponding electrical signals. Reflected and/or elicited waves may travel a path directly from the target area to the proximal array 120 elements, while others may travel to the de-matching layer, which reflects them back to proximal array 120 elements.

The proximal array 120 can be configured to detect elicited ultrasound at a frequency or range of frequencies that is different from the frequency of ultrasound projected by the distal array 110. For example, the proximal array 120 can be designed to detect and process elicited/reflected waves at one or more harmonic frequencies of the projected waves.

The arrays 110, 120 are shown as two-dimensional arrays but can also be implemented in a one-dimensional configuration or other configurations, as will be discussed further below. The array elements can be constructed of transduction mechanism elements including but not limited to piezoelectric, electrostatic, electrostrictive, magnetostrictive, magneto-electric, photo acoustic, or other mechanism for transduction to or from mechanical/pressure. The array elements may also be constructed as a microelectromechanical system (MEMS) device in the form of a capacitive micromachined ultrasonic transducer (CMUT) or piezoelectric micromachined ultrasonic transducer (PMUT) or combinations of the above.

The distal electronics 130 can be directly connected to the distal array 110 to deliver power and/or control signals to elements in the distal array 110, for example, as in the stacked configuration shown in FIG. 1B. The electronic connections for the distal array 110 elements can be made via a backside surface to the distal array 110 and/or to a common plane on a front surface of the distal array 110.

As shown in FIGS. 1A and 1B, a matching/de-matching layer 140 can optionally be disposed between the distal array 110 and the proximal array 120 to reduce propagation effects and further isolate the proximal array 120 from the distal array 110. For example, the matching/de-matching layer 140 can be constructed of a material and thickness that allows it to function as a variable frequency filter that allows ultrasonic waves generated at a first frequency by the distal array 110 to pass through, but impedes ultrasonic waves elicited and/or reflected at a different frequency from reaching the distal array 110. Indeed, the matching/de-matching layer 140 may reflect at least some of the reflected waves, at least some of which may be detected by the proximal array 120.

In one or more disclosed embodiments the matching/de-matching layer 140 can be constructed of an electrically insulating material, such as diamond, polymers, or ceramics. In an implementation of the disclosed embodiments the matching/de-matching layer 140 is constructed of one or more graphite sheets, electrically insulated to prevent electrical pathways from forming. The matching/de-matching layer 140 can further be constructed of a thermally conductive material to facilitate thermal management of the device 100. For example, in one or more disclosed embodiments the matching/de-matching layer 140 can be constructed of a material having greater thermal conductivity (anisotropic thermal conductivity) than the distal array 110 and the proximal array 120 such that heat generated in a central region of the arrays 110, 120 is conducted to an outer edge where it can dissipate and exit the device 100. Heat can also be removed from the front and back side of the device 100.

The thickness of the matching/de-matching layer 140 can be selected to maximize transmission of generated ultrasound from the distal array 110 and minimize the transmission of incident ultrasound waves to be detected by proximal array 120. The thickness of the matching/de-matching layer 140 can further be selected to maximize reflection of incident ultrasound waves to be detected by proximal array 120.

Given the frequency and the known speed of ultrasound through the matching/de-matching layer 140 material, the thickness of the matching/de-matching layer 140 can be set at or around an integral number of wavelengths divided by 4. Such a thickness would be transmissive of the generated waves and blocking/reflective of the reflected waves.

Reflected wave energy that is reflected from the de-matching layer can augment the signal created by the incident waves at the proximal array 120.

Figure 2A:
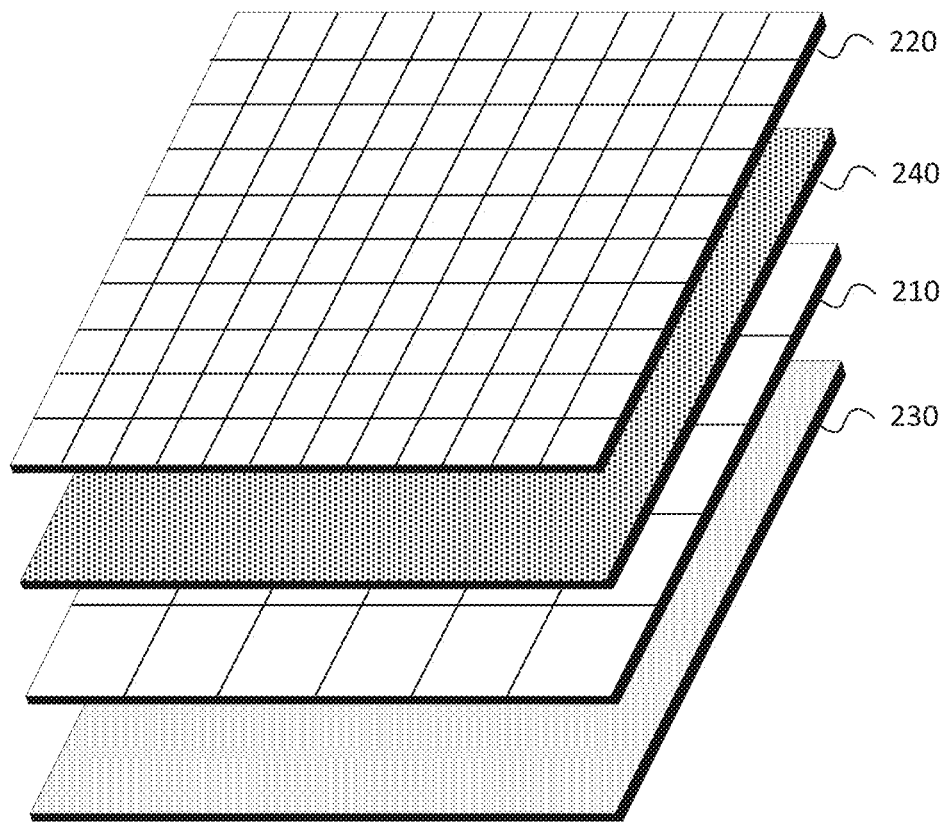
FIG. 2A shows an ultrasonic device according to another embodiment of the disclosed subject matter.
Figure 2B:
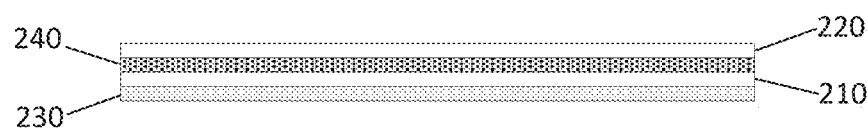
FIG. 2B shows a side view of an ultrasonic device according to another embodiment of the disclosed subject matter.

FIG. 2A depicts, by way of illustrative and non-limitative example, an exploded view of another embodiment of an ultrasonic device 200 having a stacked arrangement according to the disclosed subject matter. The disclosed device 200 includes a first transducer array 210 ("distal array") to generate ultrasonic waves, a second transducer array 220 ("proximal array"), electrically isolated from the distal array 210, to detect reactive events such as reflected ultrasonic waves, and a driving circuit 230 to supply power. The driving circuit 230 can also include a processor, microprocessor or the like to transmit control signals, execute output timing algorithms, etc. The device 200 can include a matching/de-matching layer 240, disposed between the distal array 210 and the proximal array 220. The matching/de-matching layer 240 can include electrical conductors or conduits to facilitate through-connections to the proximal array 120. FIG. 2B depicts a side view of device 200.

Elements in the proximal array 220 can be designed to include an active transduction element on a front surface and active electronics on a back surface. The fabrication of such a device may be achieved using silicon foundry techniques, with the inclusion of through-silicon vias to make connections to the active elements (e.g., capacitive micromachined ultrasonic transducers or piezoelectric micromachined ultrasonic transducers). The drive electronics can be provided on a planar surface (e.g., back or front) and fabricated using conventional techniques. This integration of the transducer and the electronics reduces the size of the device 200 and allows a greater density of transducer elements to be integrated onto a wafer (e.g., silicon, ceramics or other semiconductors). In one embodiment, electronic connections to the proximal array 220 can be made directly on a per element basis or by row column addressing and routed to the edge of the proximal array 220 for connection to the driving circuit 230. In another embodiment, electronic connections to the proximal array 220 can be combined into a serial digital stream to a lower number of connectors on the edge of the proximal array 220. Through-silicon vias (TSVs), other vias, or other methods to pass an electrical connection between the front surface and back surface of a silicon (or other semiconductor material or substrate material), or flex circuit material, or circuit board material, can also be used to facilitate the routing of the connectors on the device.

Figure 3:
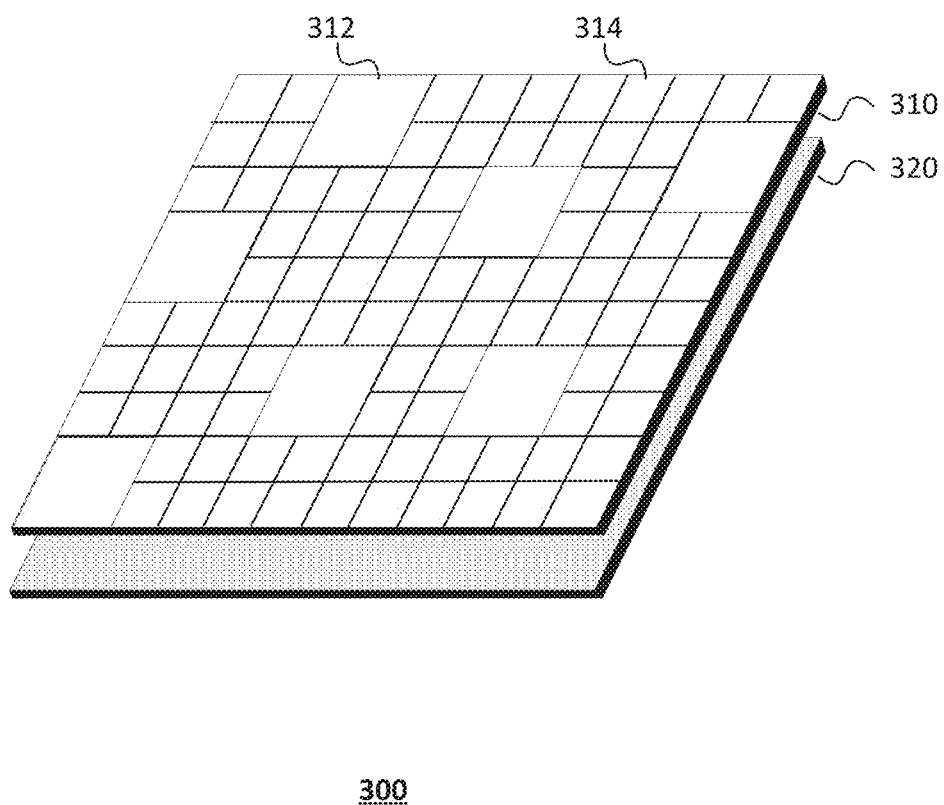
FIG. 3 shows an ultrasonic device according to yet another embodiment of the disclosed subject matter.

FIG. 3 depicts, by way of illustrative and non-limitative example, an exploded view of another embodiment of an ultrasonic device 300 according to the disclosed subject matter. The disclosed device 300 includes a transducer array 310 (combined array) that includes an interleaved mix of transmit transducer elements 312 to generate ultrasonic waves, and receive transducer elements 314, to detect incident events such as reflected ultrasonic waves, and a circuit 320 to supply power and control signals and to implement receive functionality. The transmit elements 312 can be disposed according to a regular, random or pseudorandom distribution pattern. In this embodiment the density of transducer elements 312, 314 is further reduced compared to the stacked configuration embodiments. This embodiment also includes comparatively less high energy transmit elements 312 and less receive elements 314, resulting in lower production cost and faster fabrication.

Embodiments of the disclosed subject matter such as the examples illustrated in FIGS. 1-3, can simultaneously generate therapeutic ultrasound and send it to a target area while at the same time imaging that target area by detecting lower power incident ultrasound. This improves upon conventional designs that inherently are forced to stop sending therapeutic energy to a target, wait until the sending array quiesces, and then detect returning, incident waves. The disclosed embodiments can also detect higher harmonics such that there is reduced or no interference from the projected signal. Thus, the disclosed embodiments introduce the capability of applying therapeutic ultrasound to a target area and concurrently imaging that target area.

Acoustic transducer elements are often designed to operate within a set frequency band. When used in an array, acoustic transducer elements can be controlled to activate in a pattern that collectively projects a beam of waves of energy to specific points in space (e.g., in front of the array). To form and control such a beam, a processor controls a driving circuit to vary the phase, amplitude, timing or frequency content of the output signal across the array elements in order to electronically steer the beam of sound created by the waves in a given direction. This type of operation is commonly referred to as "a phased array" operation.

In a therapy array, the processor and driving circuit utilize various timing algorithms to control the ultrasound beam profile and guide energy to a precise target region in a subject. A conventional ultrasonic therapeutic device utilizing a phased array may be operated in conjunction with an imaging device that is used to identify and monitor target regions within the subject. The imaging device ("imager") is located some distance from the transmitting phased array and may be movable to adjust the viewing area shown in the resulting images in accordance with the needs of a user of the system. The cooperation necessary between the therapy array and the imager increases the complexity of transformation calculations that must be executed in order to direct both devices to focus on the same point, and offset errors can still occur due to medium differences, e.g., differences in tissue density between the separate array paths (therapy and imager) and the intended focal point. The disclosed combined therapeutic and/or imaging device advantageously reduces the complexity of coordinated tracking operations and accounts for inhomogeneities in the path of the signal through to the focal point by virtue of its static stacked configuration using the therapeutic waves themselves to generate the imaging signal. The reduction in required calculations reduces errors and increases speed of operation compared to conventional devices.

The division of the transmitting and receiving functionality into separate arrays (e.g., 210, 220 of FIG. 2A) in the disclosed ultrasonic device advantageously eliminates the need for the quiescent period required by conventional imaging devices. Due to the physical isolation of transmit transducer elements from the receive transducer elements (and in some embodiments the isolation being further solidified by the inclusion of a matching/de-matching layer), a relatively high voltage can be applied to the transmit transducer elements without impacting the receive electronics or receive transducer elements.

Consequently, elements in each array can be optimized for specific functions related to reception or transmission. In the disclosed embodiments, transmit array elements, being separate and isolated from the receive array elements, can be optimized to output comparatively greater acoustic power than can a conventional, single-array device since the higher power usage does not affect the receive array elements. Thus, the disclosed ultrasonic device can focus a wider range of energy at a target region compared to a conventional compound transmit/receive imaging device.

Likewise, in the disclosed embodiments the receive array can be optimized for receiving functions. For example, piezo transducers can be optimized, by adjusting the size, shape, pitch, kerf, width and thickness, and/or material. Receive array elements constructed using piezo transducers can be optimized to operate at a chosen frequency, with engineered characteristics (e.g., frequency response, steering response, sensitivity response and crosstalk) that differs from the equivalent characteristics of the transmit array. It is thus possible to tune the response of the receive array to operate outside of the response of the transmit array, thus dramatically improving the signal-to-noise ratio of the device.

To further reduce noise in imaging, elements in the transmit array can be optimized to generate ultrasonic waves within a first frequency band or at a first frequency, e.g., 1 MHz, and elements in the receive array can be optimized to detect ultrasonic waves within a second frequency band or at a second frequency in a 2:1 ratio, e.g., 2 MHz, or other harmonics. In this implementation the receive array can be optimized to be nonresponsive to 1 MHz acoustic waves.

As part of the frequency tuning and optimization, the receive array elements can be formed to be smaller than the transmit array elements, e.g., a ratio size smaller, 1:2, 1:4, 1:8, etc., where "smaller" refers to a reduction in one or more dimensions (e.g., diameter, cross-section, area, thickness). Generally, thinner elements can detect higher frequencies (f~k*1/thickness), where a reduction in area or pitch increases the steering and decreases grating lobe generation. Depending on the shape of the transducer elements, ratio reductions in size can be used to arrange transducer elements in a repeating pattern while substantially maintaining transducer element border alignment between the two arrays. For example, in embodiments constructed using transducer elements having a square shape, the receive array elements can be approximately ¼ the size of transmit array elements and arranged in a repeating pattern comprising four elements of the receive array disposed substantially over a single element of the transmit array.

The disposition of receive array elements relative to transmit array elements can be optimized to reduce signal noise. In implementations of the disclosed embodiments, receive array elements can be disposed relative to transmit array elements such that borders of the elements in the two arrays are aligned, thus further reducing unwanted propagation effects.

The above described embodiments are implemented with the transmit array being beneath the receive array, however the disclosed subject matter is not limited to this configuration. In other implementations the receive array is disposed beneath the transmit array and the transmit array is constructed to be acoustically transmissive to allow reflected and/or elicited waves to pass through for detection by the receive array.

Figure 4:
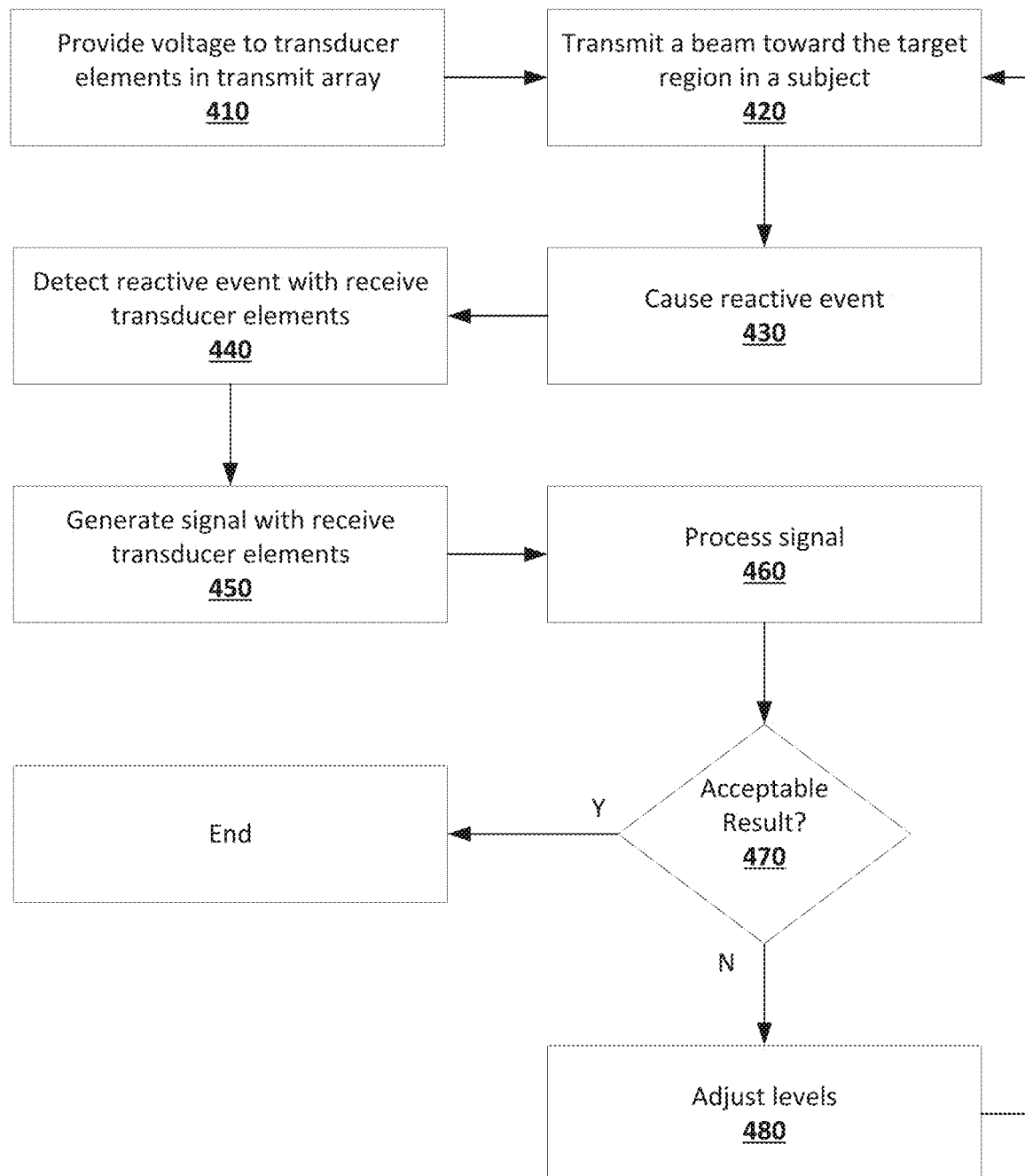
FIG. 4 show a flowchart of a method of operating an ultrasonic device according to an embodiment of the disclosed subject matter.

FIG. 4 shows an example flowchart 400 of operation for the disclosed ultrasonic device. At operation 410 the processor controls the driving circuit to send voltage signals to elements in the transmit array, for example, according to a phased array timing pattern. The processor can control the driving circuit to send voltage levels required to generate, for example, a therapeutic ultrasound beam, or an imaging ultrasound beam. Conventionally in a combined transmit/receive array the system would need to switch between the two modalities, in an alternating pattern of the two types of beams, such as a 50% therapy, 50% imaging or 75% therapy 25% imaging. The relative durations of each is dependent on the requirements for imaging (e.g., how long the imager needs to be active based on how deep the target is). In contrast, systems of the disclosed embodiments do not need to alternate between modalities. In systems of the disclosed embodiments voltage levels delivered to the transducers can be higher than voltage levels used in conventional ultrasonic imaging devices. For example, voltage levels as high as ±120 V is common (though even higher is possible) in embodiments of the disclosed system.

Although alternating modalities are not required in the disclosed embodiments, in some implementations the processor can control the driving circuit to cause the transducer array to generate pulses of ultrasonic waves in sequential patterns. In this operation mode imaging waves are distinguishable from therapeutic waves in that a therapeutic wave is generated to cause a physical change in tissue where an imaging wave is generated only to elicit reflected waves and does not cause a change in tissue. For example, to avoid tissue damage imaging waves can be carried out at either power levels less than 720 mW/cm2 or a mechanical index of less than 1.9. In this mode of operation, the processor can cause the generation of a sequential pattern such as imaging wave-therapeutic wave, therapeutic wave-imaging wave, N imaging wave-therapeutic wave, N therapeutic wave-imaging wave, etc.

An imaging wave could exceed a power level of 720 mW/cm2 or a mechanical index of 1.9, however, in such an application tissue may be altered. This type of operation could be appropriate to produce better signal-to-noise ratio or to simultaneously elicit imaging data while altering tissue.

At operation 420 the transducer elements convert the voltage into acoustic energy and transmit a beam of ultrasonic waves to a target region. The beam can be formed by short pulses of waves (from single digits to 100's) in a given frequency, for example, 1-5 MHz, or a different frequency, or the beam may be swept, such as in a chirp or gaussian distribution, or may be configured to elicit histotripsy or boiling histotripsy. The beam may also be formed from a continuous emission of waves (CW). The frequency can be selected based on the operating frequency of the receive array transducers, i.e., the frequency can be outside of the receive array elements operating range (or primary resonance) to reduce detection error. As described above, the generated ultrasonic waves can propagate in a pattern, e.g., a first pulse to deliver therapeutic energy to a target region in a subject followed by a second pulse having a lower energy or higher power level than the first pulse to deliver an ultrasonic imaging wave to the target region. A higher energy pulse may elicit harmonics that may be used for imaging.

At operation 430 the generated ultrasonic waves reach the target region and cause a reactive event. The reactive event can be, for example, ultrasonic imaging waves hitting an object in the target region and reflecting back, the ultrasonic therapeutic waves hitting an object in the target region and causing an increase in temperature, harmonics generated in the tissues by ultrasonic waves, collapses of bubbles due to ultrasonic waves, or other events such as shear waves generated by radiation force.

At operation 440 the reactive event is detected by transducer elements in the receive array. The elements can be optimized to detect a given event. For example, the elements can be designed to have an operating frequency that detects backscattered waves at a pre-determined frequency or range of harmonics derived from the transmit frequency. Some of the energy from the reactive event can be received in a direct path from the target, and other energy from the reactive event may be received from its reflection from the de-matching layer.

At operation 450 the elements in the receive array generate electrical signals corresponding to the reactive event. For example, when the reactive event is backscattered waves from the generated waves, the elements generate a signal by converting energy from the reflected waves into a voltage signal. This signal may be based on directly-received backscatter waves and also from backscatter waves that are reflected from the de-matching layer.

At operation 460 the generated signal is processed, for example, a processer can apply calculations and algorithms to resolve the signal into readable value or an image for display on a screen, or use an algorithm to determine data from the signal that indicates a material property of a target region.

At operation 470 the processor or the user determines of the process results are acceptable. For example, the processor can determine whether predetermined threshold values are met or a user can determine whether an image is in focus. If the result is acceptable then no adjustments are necessary and the image can be captured or the settings maintained to continue projecting the ultrasonic beam. If the result is not acceptable (for example the focus is not clear or the position of the detected event is not in the location that was intended to be targeted) then at operation 480 the processor or the user adjusts treatment settings for the elements, e.g., adjust the power level, focus, frequency, etc., and a refined beam is generated with the altered treatment settings at operation 420.

The mode of operation of the disclosed ultrasound device can be modified by adjusting the power delivered to the transmit array. As described above, the transmit array can produce different types of beams, e.g., focused acoustic pulses for imaging modalities, or plane wave pulses with corrections to enable high resolution plane wave imaging. In another advantage of the disclosed embodiments over conventional methods, corrections can be applied to the transmit array to correct for aberrations at the array-to-target interface and also within the target body, thus improving the quality of the images acquired. A further benefit of the disclosed embodiments is an increase in transducer frame rate (the rate at which data can be collected) by virtue of the elimination of the quiescent period, switching and settling time in conventional transmit/receive systems.

The disclosed embodiments could be compatible with magnetic resonance imaging (MRI) systems. For MR-guided high intensity focused ultrasound (HIFU) treatments it is important that the array can be used within the magnet bore so that MR imaging can be carried out during operation. To achieve this compatibility, magnetic materials such as iron and nickel can be excluded from the design, and a configuration can be utilized that minimizes or eliminates conductor loops that carry current to prevent interference with the MR sensing.

As shown above, the separation of the transmitting function and the receiving function into separate arrays allows the elements in the respective arrays to be tuned to requirements of a given application with greater versatility compared to transducers in a single combined array device. The advantages of the disclosed embodiments are applicable to various ultrasonic imaging modalities, for example, continuous wave (CW), Doppler, elastography such as Acoustic Radiation Force Imaging (ARFI), B-mode, contrast, Harmonic Imaging and Plane Wave Imaging (PWI). The disclosed embodiments could also be paired together across a subject to enable tomographic imaging from both directions. The embodiments can also be used in both high intensity focused ultrasound therapy for thermal ablation and disruption techniques such as histotripsy/boiling histotripsy or other non-linear therapies, permeation of structures and low intensity ultrasound therapy for application of localized warming.

The disclosed embodiments can acquire high resolution ultrasound images with an array that can also thermally ablate or apply other treatment modalities as required to targeted and discovered structures. For example, the receive array can image and localize structures to be ablated with the transmit array. The two arrays can be mechanically bonded with adhesive compounds or affixed with mechanical means by the application of coupling mediums to prevent voids between the two arrays, matching/de-matching layers and electrical layers. The two arrays can be tuned to operate at desired overlapping or non-overlapping frequency ranges. The transmit array can be used to generate the acoustic field for imaging, hence no offset in coordinate systems is required between the arrays.

Other applicable treatments can include localized warming for increasing the activity or the activation of therapeutic agents, the disruption or rupture of structures carrying therapeutic agents at targeted sites, activation of nerves and other neuronal structures, increasing fluid flow in venous structures through mechanical stress or otherwise, localized warming of deep tissue for physical therapy benefit, cell lysis, or the oscillation of contrast agents. When functioning in the mode of operation for histotripsy or boiling histotripsy the disclosed embodiments can perform both the imaging for localization and monitoring of treatment, as well as the application of pressure waveforms to apply the therapy portion.

The disclosed transducer element arrangement has applications not only in the field of medicine but also in the fields of non-destructive testing, industrial and biological businesses and chemical processes. The separation and optimization of the arrays for reception and transmission can implement configurations for higher resolution non-destructive imaging systems that consume less power and are more versatile. The disclosed embodiments also are useful for large scale finely controlled, industrial, chemical, biological processing. It is possible to vary, modulate or turn off the power to each element to correct for manufacturing variability, coupling inhomogeneity or underlying structure occlusions.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

The invention claimed is:
1. An ultrasonic device comprising:
   a driving circuit to provide drive power;
   a first transducer array to generate ultrasonic waves toward a target, the first transducer array being connected to receive power from the driving circuit;

a second transducer array to detect reflected or elicited ultrasonic waves traveling toward the ultrasonic device from the target, and to generate a signal based on the detected ultrasonic waves, the second transducer array being acoustically transmissive and disposed over the first transducer array such that the generated ultrasonic waves pass through the second transducer array; and a thermally conductive layer disposed between, and in contact with at least one of, the first and second transducer arrays through which heat, generated by the first and second transducer arrays, is transmitted from inner regions of the arrays to edge regions of the arrays.

2. The ultrasonic device of claim 1, further comprising a matching/de-matching layer, disposed between the first transducer array and the second transducer array, the matching/de-matching layer having a material and thickness that:

allows the generated ultrasonic waves to pass through; and impedes the reflected or elicited ultrasonic waves from reaching the first transducer array.

3. The ultrasonic device of claim 2, wherein the matching/de-matching layer is constructed of a material having greater or equal thermal conductivity than the first transducer array and the second transducer array.

4. The ultrasonic device of claim 2, wherein the matching/de-matching layer is constructed of a material having less thermal conductivity than the first transducer array and the second transducer array.

5. The ultrasonic device of claim 1, wherein transducer elements that form the second transducer array have a different frequency response than transducer elements that form the first transducer array.

6. The ultrasonic device of claim 1, wherein transducer elements that form the second transducer array have a different steering response than transducer elements that form the first transducer array.

7. The ultrasonic device of claim 1, wherein transducer elements that form the second transducer array have a different sensitivity response than transducer elements that form the first transducer array.

8. The ultrasonic device of claim 1, wherein transducer elements that form the second transducer array are of a different size and/or pitch in one or more axes than transducer elements that form the first transducer array.

9. The ultrasonic device of claim 8, wherein transducer elements that form the second transducer array are approximately ¼ the size of transducer elements that form the first transducer array.

10. The ultrasonic device of claim 9, wherein transducer elements in the second transducer array are arranged in a repeating pattern comprising four transducer elements of the second transducer array disposed substantially over a single transducer element of the first transducer array.

11. The ultrasonic device of claim 1, wherein:

the generated ultrasonic waves comprise a first pulse to deliver therapeutic energy to a region in the target followed and/or preceded by a second pulse having a lower energy level than the first pulse to deliver an ultrasonic imaging wave to the region;

the detected ultrasonic waves include waves from the ultrasonic imaging wave reflected or elicited from the target region; and the second transducer array generates the signal based on the detected waves, the signal carrying data to create an image of the target region.

12. The ultrasonic device of claim 1, wherein:

the generated ultrasonic waves from the first transducer array deliver therapeutic energy to a region in the target; and the second transducer array detects incident waves reflected or elicited from the region and generates the signal based on the incident waves, the signal carrying data to create a digital image of the target region or data that indicates a material property of the target region.

13. The ultrasonic device of claim 1, wherein the first transducer array generates the ultrasonic waves to elicit histotripsy or boiling histotripsy.

14. The ultrasonic device of claim 1, wherein:

the first transducer array generates ultrasonic waves within a first frequency band, and transducer elements in the second transducer array are substantially less sensitive to ultrasonic waves within the first frequency band than transducer elements in the first transducer array such that the second transducer array detects incident ultrasonic waves within a second frequency band different from the first frequency band.

15. The ultrasonic device of claim 14, wherein the first frequency band has a central frequency of approximately 1 MHz and the second frequency band has a central frequency of approximately 2 MHz.

16. The ultrasonic device of claim 1, wherein the first transducer array is a phased array.

17. The ultrasonic device of claim 1, wherein:

the driving circuit is disposed on a first side of the first transducer array, and the second transducer array is disposed on a second side of the transducer array opposite the first side.

18. The ultrasonic device of claim 1, further comprising receive electronics configured to process the signal generated by the second transducer array, wherein the receive electronics are substantially acoustically transparent and disposed between the first transducer array and the second transducer array.

19. A method of conducting ultrasonic therapy or ultrasonic imaging using an ultrasonic device, comprising:

disposing an acoustically transmissive second transducer array over a first transducer array such that ultrasonic waves generated by the first transducer array substantially pass through the second transducer array;

disposing a thermally conductive layer between, and in contact with at least one of, the first and second transducer arrays;

providing power to the first transducer array, the power causing the first transducer array to generate ultrasonic waves toward a target;

detecting, with the second transducer array, reflected or elicited ultrasonic waves from the target;

generating a signal, with the second transducer array, based on the detection;

creating a digital image of the target region based on the signal or determining a material property of the target based on signal; and transmitting heat, generated by the first and second transducer arrays, from inner regions of the arrays to edge regions of the arrays through the thermally conductive layer between, and in contact with at least one of, the first and second transducer arrays.

20. The method of claim 19, further comprising:
impeding the reflected or elicited ultrasonic waves from reaching the first transducer array by disposing a matching/de-matching layer between the first transducer array and the second transducer array.

21. The method of claim 19, further comprising delivering therapeutic energy, via the generated ultrasonic waves from the first transducer array, to a target region in a subject.

22. The method of claim 19, wherein providing power to the first transducer array comprises:
providing a first signal to the first transducer array to cause the first transducer array to deliver therapeutic ultrasonic energy to a target region in a subject; and
providing a second signal to the first transducer array, the second signal having a lower energy level than the first signal, to cause the first transducer array to deliver an ultrasonic imaging wave to the target region.

23. The method of claim 22, where the first signal is provided sequentially before the second signal.

24. The method of claim 22, where the second signal is provided sequentially before the first signal.

25. The method of claim 22, further comprising:
detecting, with the second transducer array, incident waves from the ultrasonic imaging wave that are reflected or elicited from the target region; and
generating, with the second transducer array the signal based on the incident waves, the signal carrying data to create an image of the target region or data that indicates a material property of the target region.

26. The method of claim 19, wherein:
transmitting the generated ultrasonic waves within a first frequency band from the first transducer array, and
detecting, with the second transducer array, reflected ultrasonic waves within a second frequency band different from the first frequency band.

27. The method of claim 19, wherein the first frequency band has a central frequency of approximately 1 MHz and the second frequency band has a central frequency of approximately 2 MHz.

* * * * *